United States Patent
Brinkmann

(10) Patent No.: US 9,005,261 B2
(45) Date of Patent: Apr. 14, 2015

(54) APPARATUS FOR GENTLE LASER TREATMENT OF THE RETINA

(75) Inventor: Ralf Brinkmann, Luebeck (DE)

(73) Assignee: Medizinisches Laserzentrum Luebech GmbH (DE)

( * ) Notice: Subject to any disclaimer, the term of this patent is extended or adjusted under 35 U.S.C. 154(b) by 999 days.

(21) Appl. No.: 12/740,530

(22) PCT Filed: Oct. 24, 2008

(86) PCT No.: PCT/DE2008/001722
§ 371 (c)(1),
(2), (4) Date: Aug. 4, 2010

(87) PCT Pub. No.: WO2009/056099
PCT Pub. Date: May 7, 2009

(65) Prior Publication Data
US 2010/0292763 A1 Nov. 18, 2010

(30) Foreign Application Priority Data
Oct. 31, 2007 (DE) .......................... 10 2007 052 103

(51) Int. Cl.
*A61F 9/008* (2006.01)
*A61B 18/20* (2006.01)
*A61B 17/00* (2006.01)
(Continued)

(52) U.S. Cl.
CPC ................. *A61F 9/008* (2013.01); *A61B 18/20* (2013.01); *A61B 2017/00084* (2013.01); *A61B 2017/00106* (2013.01); *A61B 2018/00636* (2013.01); *A61F 9/00821* (2013.01); *A61F 9/009* (2013.01); *A61F 2009/00844* (2013.01); *A61F 2009/00863* (2013.01)

(58) Field of Classification Search
CPC ............... H01S 3/00; H01S 3/10; H01S 3/11; H01S 3/13; H01S 3/113; H01S 3/117; H01S 3/121; H01S 3/123; H01S 3/098; A61N 5/06; G01N 25/02; G05B 13/02; G01P 35/00; G01C 25/00; G06F 19/00
USPC ................. 372/1–32; 607/88–95; 374/17–20; 700/28–34, 44–47; 702/85–107
See application file for complete search history.

(56) References Cited

U.S. PATENT DOCUMENTS 4,689,482 A * 8/1987 Horikawa et al. ............. 250/205
4,741,612 A * 5/1988 Birngruber et al. ........... 351/221
(Continued)

*Primary Examiner* — William Thomson
*Assistant Examiner* — Victor Shapiro
(74) *Attorney, Agent, or Firm* — Livingston Loeffler, P.A.; Edward M. Livingston, Esq.; Bryan L. Loeffler, Esq.

(57) ABSTRACT

A therapeutic laser with a source of pulsed electromagnetic radiation, a control device for controlling the intensity and/or the duration of the therapeutic laser applied to the tissue, and a detection device for detecting optoacoustic signals triggered by irradiating the living tissue with the pulsed electromagnetic radiation. The therapeutic laser is characterized by an evaluation device that acts on the control device and is used for calculating a degree of quality B(t) from the optoacoustic signals detected by the detection device for individual laser pulses applied to a predetermined laser spot and determining a fit function f(t) at a predetermined point in time $\Delta t1$, the fit function f(t) approximating the mean curve of B(t) for $0 \leq t \leq \Delta t1$. The intensity and/or the irradiation time of the therapeutic laser is defined by the parameters for the predetermined laser spot, the parameters being determined for the fit function f(t).

20 Claims, 4 Drawing Sheets

(51) Int. Cl.
*A61B 18/00* (2006.01)
*A61F 9/009* (2006.01)

(56) References Cited

U.S. PATENT DOCUMENTS

| | | | | |
|---|---|---|---|---|
| 5,978,391 | A * | 11/1999 | Das et al. | 372/20 |
| 6,078,599 | A * | 6/2000 | Everage et al. | 372/20 |
| 6,322,555 | B1 * | 11/2001 | LaHaye | 606/5 |
| 6,585,722 | B1 * | 7/2003 | Abe | 606/4 |
| 6,671,043 | B1 * | 12/2003 | Huettman | 356/300 |
| 6,830,567 | B2 * | 12/2004 | Schuele et al. | 606/4 |
| 2006/0241572 | A1 * | 10/2006 | Zhou | 606/7 |
| 2007/0073905 | A1 * | 3/2007 | Cynthia et al. | 710/1 |
| 2007/0213693 | A1 * | 9/2007 | Plunkett | 606/6 |

\* cited by examiner

APPARATUS FOR GENTLE LASER TREATMENT OF THE RETINA

FIELD OF THE INVENTION

The invention relates to a laser apparatus for treating living tissue, in particular the retina of the living eye, the effect of laser irradiation being monitored automatically during processing and being used for controlling the laser.

BACKGROUND OF THE INVENTION

Laser photocoagulation of the retina has been practiced for more than 30 years. Its therapeutic success is undisputed, being founded on many studies for different retinal diseases. The uses of the laser are both therapeutic (for example diabetes, thromboses of the eye, age-related macula degeneration (AMD)) and preventive (for example retinopexy). For photocoagulation, according to the type of disease, between a few single expositions in the macula and up to 3000 foci are applied in the case of pan-retinal photocoagulation. According to the spot size, 100-500 mW laser power is applied within 50-300 ms per focus. Mainly lasers in the green spectral range (Ar-ion lasers with 514 nm or frequency-doubled Nd-lasers at 532 nm) are used, but also lasers and laser diodes in the near IR-range.

The only dosage of laser photocoagulation employed so far consists in subsequently checking the ophthalmologic appearance of the coagulation site at the fundus. That the retina turns grey or white in the process, shows an irreversible thermal necrosis of the neuronal retina that can reach, depending on the intensity and extent of the coagulation, the entire retina from the retinal pigment epithelium (RPE) via the photoreceptors to the nerve fiber layer and can also include necroses of all uvulas. The large spatial extent of the coagulation effects results from the thermal conduction from the melanine-containing absorbing layers into the neighboring tissue layers.

The pan-retinal laser coagulation of the retina is the most common use of the laser in ophthalmology. Here the inner layers of the peripheral retina are to be destroyed thermally in 3-10 sessions with up to 3000 laser foci of different size so as to prevent the unchecked vessel growth and the blindness connected thereto at a later point. With most patients the laser treatment is extremely painful. Only a retrobulbar injection can avoid pain. This however entails that the mobility of the bulbus that is necessary for carrying out the photocoagulation in the periphery is switched off: in the case of over-coagulations and in particular in the case of repeat treatments, additional thermal damage of ganglion cell layers is to be feared that can lead to extensive defects of the field of vision.

Since the absorbing granula vary considerably in terms of their local and spatial density it is not surprising that the histological results after laser coagulation can vary considerably even in the case of identical exposition parameters. The extent of the damage essentially is a function of the extent of the laser-induced rise in temperature. In practice, it cannot be predicted due to different pigmentation and thus absorption of the retina both inter- and also intraindividual.

Automatic, temperature-controlled online dosimetry for laser treatment with minimal invasive damage is a goal to be desired that cannot be achieved through the application method that is conventional at the moment for ophthalmoscopic examination.

Physics offers different methods for measuring temperatures, however almost all of them are practically unsuitable for measuring the ocular fundus.

Invasive measurement methods as for example thermal probes or dyes that fluoresce as a function of the temperature are too annoying—among others on account of side effects—and/or too imprecise. Due to the absorption of the thermal radiation in the eye, thermal imaging cameras cannot be used.

Methods that are based on auto-fluorescence seem to be suitable, as is for example taught by DE 102 40 109 A1, but a uniform distribution of the chromophores that does not exist in practice is a precondition here.

The analysis of temperature-dependent, thermo-mechanical expansion of an absorber and the pressure wave emitted therewith after the application of a short laser pulse has been described in Sigrist M. W., "Laser Generation of Acoustic Waves in Liquids and Gases", Journal of Applied Physics 60(7):R83-R121, 1986. On this basis the optoacoustic temperature measurement on the retina was developed as it is illustrated in DE 101 35 944 C2. Additional, repetitive irradiation with short laser pulses produces pressure transients whose amplitude can be recorded with an ultrasound sensor (for example piezo element) that is integrated into the contact lens required for laser treatment anyway. The instantaneous increase in temperature can be determined from the amplitude. In the process, the dependency of the temperature on the choroid perfusion and the light absorption and thus the absolute necessity of an online dosimetry based on the temperature could be illustrated.

The method of DE 101 35 944 C2 was previously used for temperature measurements in Transpupillary Thermotherapy (TTT) and the Selective Retina Therapy (SRT). In the case of SRT, the treatment pulses themselves can be used for determining the temperature. WO 2005/007002 A1 further describes strategies that use the optoacoustic signal for controlling the therapeutic laser. WO 2005/007002 A1 however assumes that microscopic bubbles will form sooner or later due to the laser impact. Such bubbles significantly change the behavior of the pressure transients and thus serve to identify the damage threshold in the vicinity of which the laser should operate. This is then realized by a suitable feedback.

In laser photocoagulation, only maximum temperatures of 40-80° C. are realized for treatment of the ocular fundus. Bubble formation cannot set in below 100° C., so that this cannot be any option for laser control.

The aim of photocoagulation is the thermal denaturation of proteins and tissue. It is in particular the dependency of the extent and depth of damage of coagulations of the retina that has been well researched experimentally and theoretically using different laser parameters (e.g. Birngruber R, Hillenkamp F, Gabel V P., "Experimental studies of laser thermal retinal injury", Health Phys 44(5):519-531, 1983 or Birngruber R, Hillenkamp F, Gabel V P., "Theoretical investigations of laser thermal retinal injury", Health Phys 48(6):781-796, 1985). The findings are that the damage to the tissue is both a function of the duration of the laser irradiation and also directly—and particularly critically—of the temperature increase caused during this period. Here the damage integral $\Omega$ describes a certain change that is a function of damage criteria and tissue and that is influenced by the temperature curve T(t) over the total duration of the temperature increase $t_s$.

$$\Omega(t_s) = A \cdot \int_0^{t_s} dt \cdot T(t) \cdot e^{-\frac{\Delta E}{k \cdot T(t)}}$$

The activation energy $\Delta E$ and the frequency factor A can be determined experimentally, in that the threshold for thermal damage for different temperature increases and exposition times are determined, k designating the Boltzmann constant. The constants differ for many tissues. $\Omega$ is influenced exponentially by the temperature and approximately linearly by the time. This means that the effects of an excessive temperature can be far more serious than that of an irradiation period that is too long. To describe a stronger denaturation, $\Omega \gg 1$ is selected (e.g. $\Omega=100$), if the value clearly stays below $\Omega=1$, $\Omega \ll 1$, no thermal changes are to be expected.

SUMMARY OF THE INVENTION

It is the object of the invention to specify a laser apparatus for retina treatment that uses optoacoustic signals for controlling the exposition parameters of the laser irradiation so that a pre-selected change (damage) of the tissue is achieved that is identical at each laser spot.

The object is achieved by an apparatus having the features of claim 1. The sub-claims specify advantageous embodiments. Here it is particularly advantageous to provide an apparatus for treating living tissue with a laser, comprising a therapeutic laser with a source of pulsed electromagnetic radiation, a control device for controlling the intensity applied to the tissue and/or the irradiation duration of the therapeutic laser, and a detection device for detecting optoacoustic signals triggered by irradiating the living tissue with the pulsed electromagnetic radiation, in which an evaluation device that acts on the control device and is used for calculating an evaluation measure B(t) for individual laser pulses on the basis of the optoacoustic signals detected by the detection device, and for determining a fit function f(t) at a predetermined point in time $\Delta t_1$ approximates the mean curve of B(t) for $0 \leq t \leq \Delta t_1$ with a slope different from zero, the laser intensity and/or the irradiation time of the therapeutic laser being defined by the parameters determined for the fit function f(t).

The invention described below is suitable for controlling the general therapy—that is to say for processing any living tissue—, if an optoacoustic signal that can give information on the present state of the tissue is generated and measured during processing. Therefore the application of the invention is not limited to ophthalmology and not only to laser therapies but is predominantly seen there at present. Below only the laser treatment of the ocular fundus is dealt with.

The basic idea of the invention, based on the measurement setup suggested in DE 101 35 944 C2, consists in estimating an irreversible change in tissue caused thermally before it actually occurs. This is achieved by continuously monitoring the optoacoustic signal and realizing a feedback. In the application of the invention, it is in particular not necessary to determine temperatures or to calculate them from data. Only the temporal change of the pressure transients is detected and used for the control purposes.

The inventive apparatus has at least the following components:
- A laser light source for therapeutic radiation (in the following therapeutic laser)
- A control unit for the therapeutic laser for controlling the radiation intensity (radiation power and beam diameter) that impacts on the tissue and/or the radiation duration (in the following irradiation parameter),
- A detection device for recording pressure transients that are produced by pulsed irradiation of the retina,
- An evaluation device with an internal timer and an electronic data storage unit that constantly records the pressure transients and decides the irradiation parameters to be adjusted by the control unit, by comparing in step with values listed in table form in the data storage unit.

BRIEF DESCRIPTION OF THE DRAWINGS

The individual components and the functioning are explained in more detail also with reference to the following figures.

DESCRIPTION OF THE PREFERRED EMBODIMENTS

Figure 1:
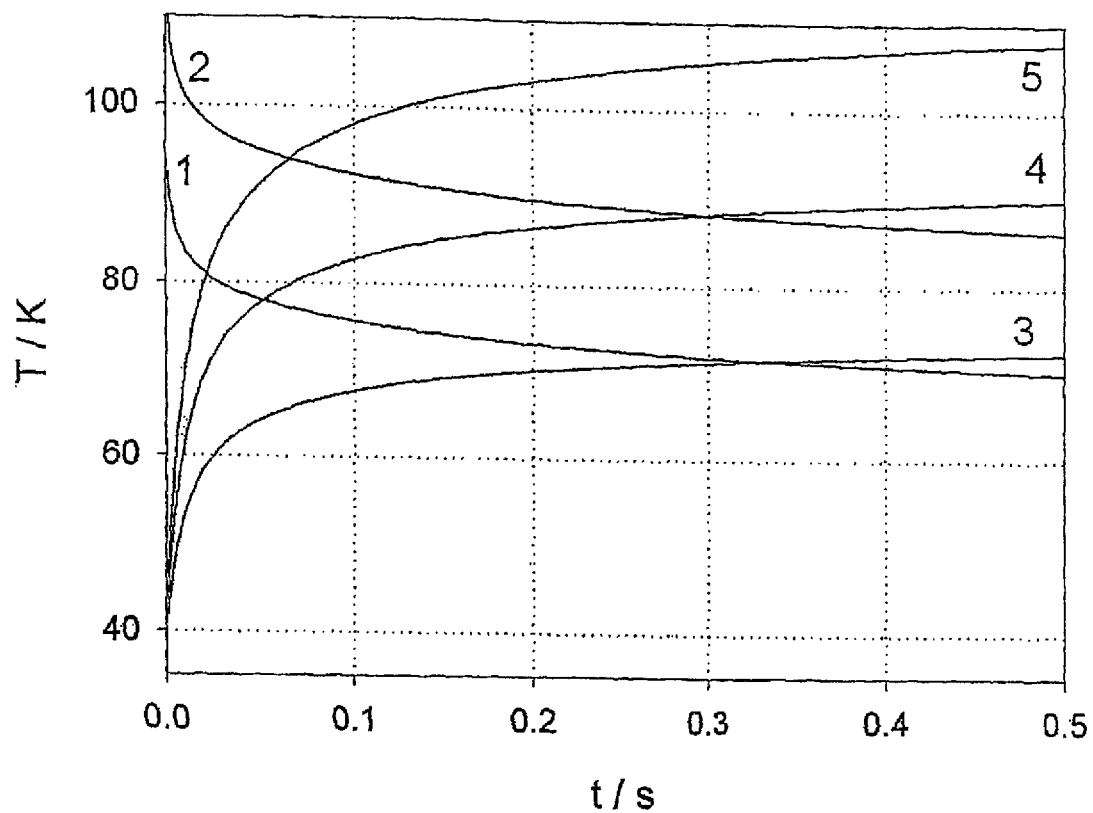
FIG. 1 shows the temperature-dependent curve of the Arrhenius parameter of the retina (damage integral $\Omega$, from the literature) for $\Omega=1$ (curve: 1, optically visible threshold) and $\Omega=100$ (curve: 2, clear coagulation) and the calculated temperature rise for irradiation of a 200 μm spot with different laser powers in the green spectral range at the center of the retinal pigment epithelium as the strongest absorber (curve 3: 20 mW, curve 4: 30 mW, curve 5: 40 mW) assuming identical absorption.

The therapeutic laser can be designed as a cw laser or as a repeatedly pulsed laser so that optoacoustic measurements can be carried out at all, pulsed electromagnetic radiation must of necessity be applied to the retina, preferably precisely to the laser spot treated by the therapeutic laser. These radiation pulses per se only have to provide for rather small temperature variations (less than 1° C.), to produce pressure waves that can be measured. Therefore they can be irradiated from a second probe laser that is completely independent from the therapeutic laser (cf. DE 101 35 944 C2), both beams being preferably mirrored into the same beam path. In actual fact, using a laser for producing the optoacoustic signal is in no way imperative. A broad-band light source with pulsed operation (for example SLD, superluminescent diode) or a repeating flashlight can be used as well (in principle even modulated microwaves or X-rays were possible, but preferably not on the eye). A precise delimitation of the pulsed excitation radiation to the therapeutic laser spot is favorable, but not at all necessary.

A repeatedly pulsed therapeutic laser (e.g. pulse power 100 watts, pulse duration around 100 ns, repetition rate about 10 kHz, on/off ratio approximately 1:1000) is however on its own sufficient for realizing the invention. The effect of such a "nanopulsing" laser on biological tissue can be compared to that of cw irradiation, but each individual pulse produces a short-term temperature increase in the tissue by fractions of one degree Centigrade. This entails pressure waves due to the material expanding, that can likewise be detected using the pressure sensor.

In the following text it is always assumed that the therapeutic laser has been designed to apply repeatedly pulsed laser light onto the retina independently of the fact whether or not it is supplied with it from an additional probe laser light source. Even a cw laser with a chopper can be considered. For simplification reasons, other designs of the therapeutic laser, for example using flashlights etc., are not discussed any further. That the functioning described further below can be transferred to such designs will be readily obvious to the person skilled in the art.

The control unit comprises all means known per se to change the beam of the therapeutic laser, that is to say in particular means for checking the pump power or even an acousto-optic modulator that deflects a proportion of the emitted laser light from the beam path toward the retina, and drivable beam optics that can in particular widen the beam. Laser power, beam diameter, and irradiation time are the parameters to be regulated, that control the tissue damage to be achieved.

The detection device is preferably designed as an ultrasound converter that is arranged on the requisite contact lens and reacts to pressure fluctuations by generating electrical signals. The signals are proportional to the pressure amplitude and are fed to the evaluation device. It shall be remarked at this point that there are still other possible embodiments of the detection device, in particular those for non-contacting measurements. They are not covered here in more detail, but the present invention should not be regarded as being limited to a specific type of measurement of the pressure transients.

The new aspect of the inventive apparatus is in the type of evaluation of the recorded signals by the evaluation device. The latter has two tasks to fulfill:
1. The pressure transients are sampled by the detection device as functions of the time and transmitted to the evaluation device. The evaluation device continually measures the time that has elapsed, as long as the therapeutic laser irradiates the retina. For each pressure transient that is caused by a single light pulse it calculates an auxiliary parameter that is to be referred to here as an evaluation measure. The maximum amplitude or the surface area below the pressure transient curve (for example absolute integral) can be considered as the evaluation measure, but also phase shifts and frequency changes of the pressure transients inform on the state changes of the tissue due to the impact of the therapeutic radiation. It has been shown that these parameters on average correlate well with the temperature of the ocular fundus, e.g. pressure and phase changes are proportional to temperature changes over short distances. Since a value of the evaluation measure of the pressure transients is formed for each light pulse, the evaluation measure then exists in a first interval of duration $\Delta t_1$ as a function of time B(t). This first interval starts with the onset of the therapeutic radiation (=start of the time measurement) and be referred to as "startup phase".
2. Usually, B(t) is initially very noisy and is smoothed as required by the evaluation device by means of a smoothing procedure, for example by means of window averaging with a window width very much smaller than $\Delta t_1$.

The smoothed function <B(t)> is fitted at the end of the startup phase using a conventional procedure (e.g. least squares or similar) by a simple analytical function that estimates in advance the future course of the evaluation measure by extrapolation while maintaining current irradiation parameters. The evaluation device compares the fit parameters that have been found for the simple analytical function with data listed in tables in the internal data storage unit. On the basis of this comparison, the control unit is driven to match the irradiation parameters.

In the following text, the functioning of the inventive apparatus is explained in more detail. After a few preliminary remarks, specific designs of the invention are illustrated.

FIG. 1 represents curves for the temperature-time dependency of the denaturation of proteins in the retina from the literature (curves 1 and 2). Both curves show isolines with an identical extent of the damage (curve 1: $\Omega=1$, coagulation that is just visible; curve 2: $\Omega=100$, strong coagulation) as a function of the selected exposition parameters (here: temperature and time). FIG. 1 also shows the temperature rise, calculated assuming identical absorption, when a 200 µm spot is irradiated with varying laser powers in the green spectral range at the center of the retinal pigment epithelium as the strongest absorber (curve 3: 20 mW, curve 4: 30 mW, curve 5: 40 mW). The calculation does not take into account any change in the tissue.

Figure 2:
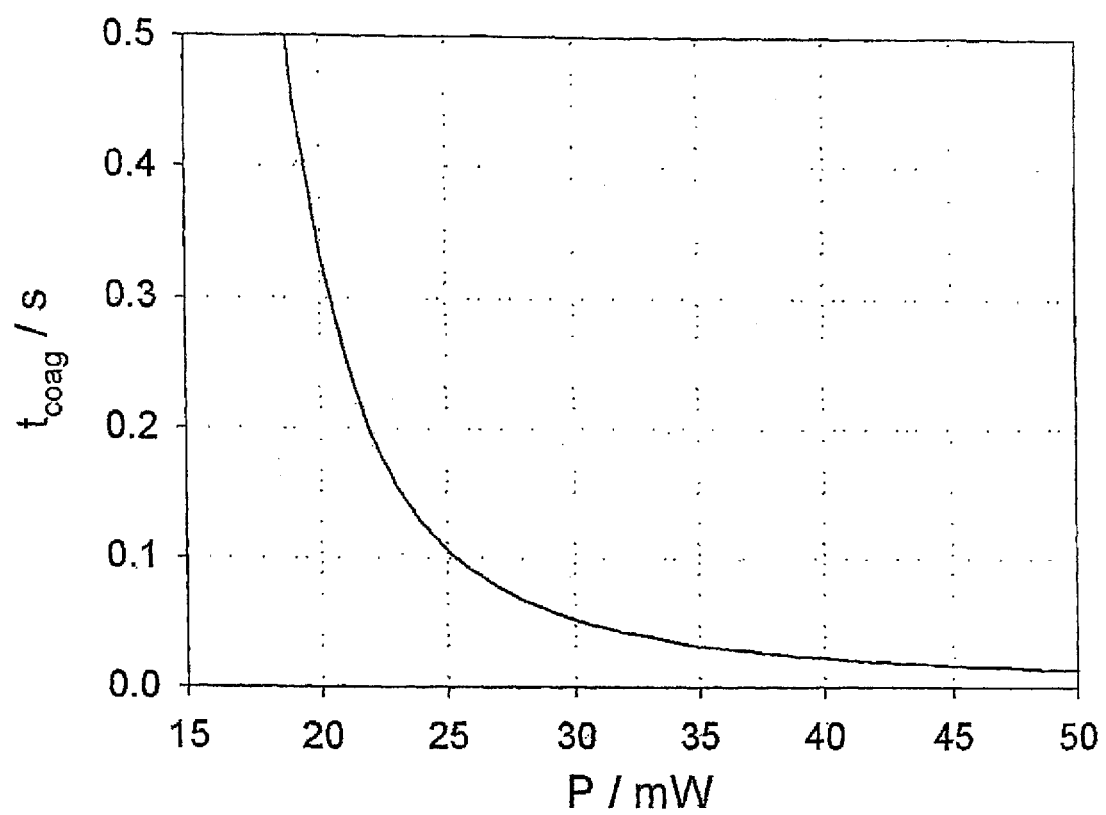
FIG. 2 shows the irradiation time until the threshold ($\Omega=1$) has been reached, that is necessary for the respective power (as for FIG. 1) in the case of a spot diameter of 200 μm, assuming identical absorption.

The $\Omega$ family of curves (1, 2) and the family of curves (3, 4, 5) obviously intersect sooner or later, and in particular the intersection points with curve 1 specify those times for the different laser powers when coagulation is first visible. To better illustrate this, FIG. 2 shows the dependency of this time $t_{coag}$ on the laser power as a curve.

Figure 3:
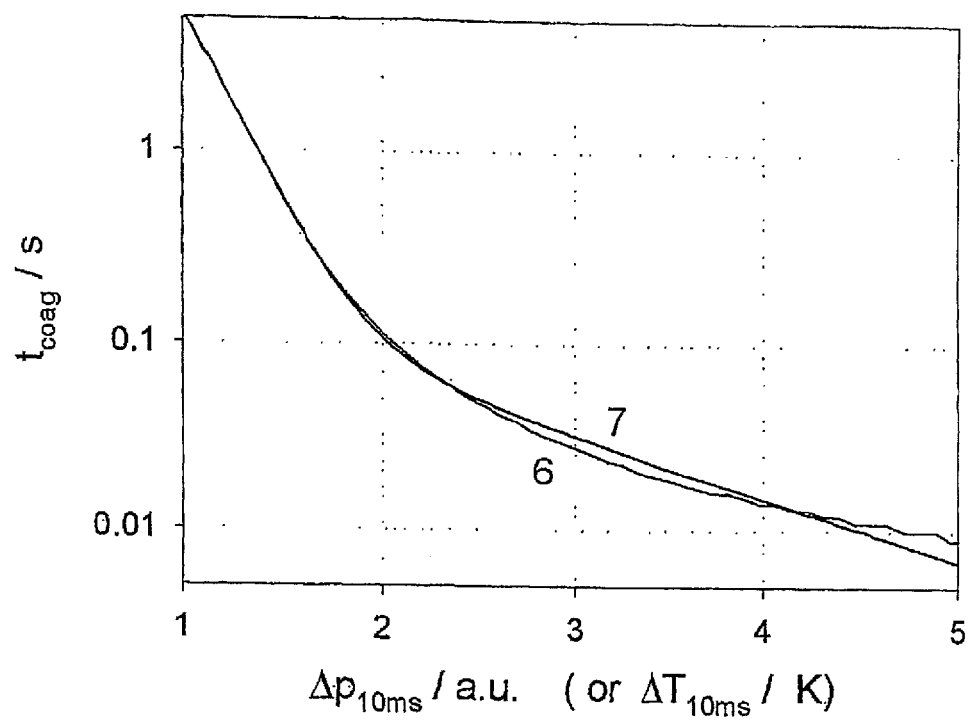
FIG. 3 shows the coagulation start ($\Omega=1$) to be expected compared to the rise in the pressure amplitude after 10 ms (curves 6 and 7). Only for reasons of understanding, the temperature rise after 10 ms derived from FIG. 1 is plotted in addition on the abscissa, since $\Delta p \sim \Delta T$.
Figure 4:
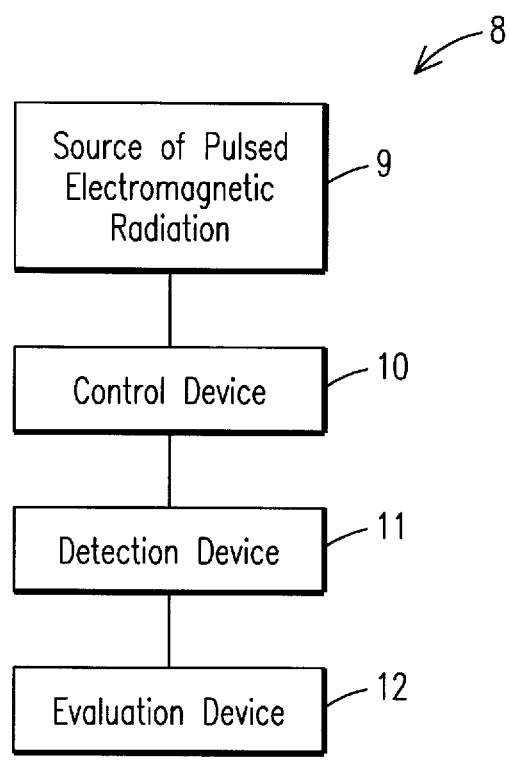
With reference to FIG. 4, a box diagram of a therapeutic laser 8 of the present invention is illustrated. The therapeutic laser 8 has a source of pulsed electromagnetic radiation 9, a control device 10 for controlling the intensity applied to the tissue and/or the irradiation duration of the therapeutic laser, and a detection device 11 for detecting optoacoustic signals triggered by irradiating the living tissue with the pulsed electromagnetic radiation, in which an evaluation device 12 that acts on the control 10 device and is used for calculating an evaluation measure B(t) for individual laser pulses on the basis of the optoacoustic signals detected by the detection device, and for determining a fit function f(t) at a redetermined point in time $\Delta t_1$ approximates the mean curve of B(t) for $0 \leq t \leq \Delta t_1$ with a slope different from zero, the laser intensity and/or the irradiation time of the therapeutic laser being defined by the parameters determined for the fit function f(t).

With the same degree of absorption, different laser powers lead to different temperature rises shortly after switching on the therapeutic laser. As an alternative, FIG. 3 therefore shows the time $t_{coag}$ as a function of the temperature increase (curve 6). Since the Grüneisen coefficient can be approximated linearly very well over small temperature ranges, the change in the pressure amplitude $\Delta p$ is plotted on the abscissa in FIG. 3 and can be measured directly. (Reminder: The pressure amplitude is a possible evaluation measure of the pressure transient.) Converting into temperatures is thus not necessary. Even if the second approximation (parabolic development of the temperature with the pressure) is considered, the times change only little up to coagulation (curve 7).

The pressure rise up to the start of the treatment is therefore a direct measure for the time when coagulation sets in. The speed of this increase cannot be predicted before the start of the irradiation if the material properties are not precisely known at the selected location of the laser spot (this is always the case in particular for retina tissue).

From the course of the evaluation measure during the startup phase in which as yet no tissue changes occur, there results according to the invention a sensible estimation of the total time until coagulation, by extrapolation and determining intersection points with the previously known $\Omega$ curves that describe the extent of the damage. The $\Omega$ curves exist for example as value tables in the data storage unit of the evaluation device that carries out the fitting procedure and calculates the intersection of the fit curve with a selected $\Omega$ curve. Since this calculation takes place immediately after the initial phase, the result is the residual time until the desired tissue damage is reached.

In a first embodiment of the invention, the evaluation device controls the control device after the pre-calculated residual time has expired and causes the therapeutic laser to be switched off.

The treating physician can preferably reactivate the therapeutical laser only manually, generally after the change to another laser spot. The extent of the desired tissue damage can be selected by the physician prior to the start of the treatment by manually programming the evaluation device. Preferably he selects a $\Omega$ value, being guided by a menu.

The first design of the invention proceeds from two basic requirements:
1. A body of evidence has to exist on the course of the $\Omega$ family of curves, for example from literature or from one's own preliminary examinations that may possibly also be costly. Here the Arrhenius model discussed in the prior art does not represent the only possibility to define tissue damage. In particular it can be convenient for different clinical pictures or therapeutical approaches to determine totally different models or new value tables and to store them in the memory of the evaluation device. Ultimately, prior to the therapeutical usage of the apparatus the family of curves must have been determined empirically and sufficiently precisely for the evaluation measure to be considered in each case.
2. Since the fitting procedure of the evaluation device is to serve for extrapolation of <B(t)> after the starting phase, a reasonable fit function has to be pre-specified. A selection that makes sense physically is one that ensures that the fit function approaches a finite end value for large exposition times. What is being suggested specifically here, is the function $$f(t)=a-b\exp(-\lambda t) \text{ with } a, b, \lambda \text{ as fitting parameters.} \quad (1)$$

It starts at t=0 (start of the therapeutic radiation) with the starting value a−b, has an initial slope of b$\lambda$ and slowly approaches the end value a. The fitting parameters are easy to determine from the values of <B(t)> determined during the starting phase, so that as a good approximation $$<B(t)>\approx f(t) \text{ holds for } 0\leq t\leq \Delta t_1 \quad (2)$$

The evaluation device now calculates the intersection of f(t) with the preselected $\Omega$ curve from the data storage unit and calculates the time $t_{coag}>\Delta t_1$ when the therapeutic laser is to be switched off. This time obviously depends on the choice of the fit function f(t) that could well also have another shape. For example, also a polynomial could be considered. Here again, it may be favorable to use different fit functions for different therapeutical purposes and/or clinical images.

Even if the inventive apparatus, presented up till now, is used, there remains a certain degree of uncertainty as to the tissue damage that has been actually achieved. However, this uncertainty is considerably reduced relative to the measures according to the state of the art—visual inspection by the physician.

A further improvement can be achieved with a second design of the invention. According to what has been said previously, an optimum fit function f(t) can be determined unanimously at most in the individual case. When it is selected, it is still possible to over- or underestimate systematically the true development of the evaluation measure, so that the therapeutic radiation is then always applied for too short or too long a time. This entails that the tissue damage can be particularly different between two laser spots that differ strongly in terms of their absorption—and thus in their initial slope of the evaluation measure.

According to the invention, a repeatable measurement and evaluation process is additionally provided. For the fitting parameters determined during the initial phase it is checked whether the course of f(t) corresponds to a predetermined positive criterion. If yes, lasering is continued as described above, otherwise the laser power is changed.

The positive criterion is to be in particular that during the temporal range of the initial phase $\Delta t_1$ the calculated fit function is completely inside a predetermined corridor, that is to say only a limited selection of initial courses is permitted. In particular the initial slopes (e.g. according to equation (1): WO is limited to a specific range of values, but also the curvature behavior of f(t) can be restricted in such a way. The restriction makes sense in particular so as to keep the irradiation times within certain limits. Thus it is known for example that irradiation times that are too long (several 100 ms) entail the risk of involuntary eye movements of the patient. In particular during the laser therapy in the area of the macula, this is what you want to avoid. If, however, the inventive measurement of the initial slope of the evaluation measure suggests that only a very short irradiation time (e.g. <30 ms) would be necessary for coagulation, then due to the then very rapid heating-up and the start of the vaporization the risk of retinal bleeding would exist, as is well documented in the literature for pulse durations of a few milliseconds.

If during the initial phase the calculated fit function does not keep to the corridor that is preferably stored for comparison reasons in the data memory, for example in the form of two limit functions $f_{min}(t)$ and $f_{max}(t)$ between which f(t) may move, the therapeutic laser is preferably deactivated until the tissue has cooled down again to its starting temperature. Since the initial phase is only short, this happens very rapidly and the tissue has not yet suffered any damage. The evaluation device commands the control device to increase the power of the therapeutic laser if the fit function leaves the corridor in the downward direction, or otherwise to reduce it. The extent of the power matching should preferably be geared to the extent of the deviation between fit function and corridor. The most simple, convenient matching consists in multiplying the laser power with the ratio of the average desired slope of the evaluation measure (which is indeed prescribed) and the slope actually measured at the laser spot. It is also the radiation intensity (power/surface area) that can be changed instead of the laser power by appropriately widening or narrowing the beam.

If the therapeutic laser is ultimately reactivated, the measurement and evaluation process above starts from scratch at the same laser spot with the power that has now been changed. The matching steps are repeated until the positive criterion is finally fulfilled. Reactivation of the therapeutic laser has to take place fully automatically between the different matching procedures of the laser power—in contrast to the manual activation mentioned above during a transition from one laser spot to the next one. The apparatus can set different powers within fractions of a second and "test" it on the retina. The treating physician does not see the automatic process and all the while keeps the applicator pointed only at the therapeutical location selected by him. If he had to activate the therapeutic laser himself, he would most likely shift the laser spot due to the movement and matching would possibly never succeed.

A special case of the previous design with iterative matching of the laser intensity (power and/or irradiation surface) is the one-step iteration that should get a special mention. Here, if a deviation of the starting course of the evaluation measure from the predetermined corridor is established, no deactivation of the therapeutic laser is carried out. The power of the therapeutic laser is instead matched during current operation—as described by multiplication with a ratio value. The time $t_{coag}$ until the onset of the coagulation is not calculated separately here, but results from the pre-known course of the desired curve, e.g. in the center of the corridor, i.e. it is predetermined.

This special design of the invention is certainly somewhat less precise than the above-described apparatus with iteration, because it dispenses with a check of the success of the control measure and its optimization. However, it has the advantage that it guarantees that the treatment duration of a single laser spot corresponds to that which is common nowadays.

In contrast thereto, the iteratively operating apparatus safely provides for an approximation of the evaluation measure to the desired course or the corridor. In practice, the absorptivity present at the current laser spot is measured, and fully-automatically matching the laser power leads to the energy deposition taking place in all laser spots in the same way, in particular with the same temporal course. Herein is seen the presently best-possible guarantee to effect a constant damage during the entire treatment.

The invention claimed is:

1. Apparatus for treating a retina of a living eye with a laser, comprising
a therapeutic laser with a source of pulsed electromagnetic radiation,
a control device for controlling the intensity applied to the tissue and/or the irradiation duration of the therapeutic laser, and
a detection device for detecting optoacoustic signals triggered by irradiating the living tissue with the pulsed electromagnetic radiation, wherein
an evaluation device connected to the control device is used for calculating an evaluation measure $B(t)$ for individual laser pulses on the basis of the optoacoustic signals detected by the detection device, and
for determining a fit function $f(t)$ at a predetermined point in time $\Delta t_1$, that fit function $f(t)$ approximating the mean curve of $B(t)$ for $0 \le t \le \Delta t_1$ with a slope different from zero, wherein $0 \le t \le \Delta t_1$ is a startup phase in which as yet no tissue changes on the retina occur,
the laser intensity and/or the irradiation time of the therapeutic laser being defined by the parameters determined for the fit function $f(t)$.

2. Apparatus according to claim 1, characterized in that the laser intensity and/or the irradiation time of the therapeutic laser are jointly defined by the parameters determined for the fit function $f(t)$ and a predetermined value table, stored in a data storage unit, for $F(\Omega, t)$, $\Omega$ being a measure for the tissue damage.

3. Apparatus according to claim 2, characterized in that the control device is set up to switch off the therapeutic laser after the time $t_{coag} > \Delta t_1$ that results from the condition $f(t_{coag}) = F(\Omega_0, t_{coag})$ when an intended tissue damage $\Omega_0$ is specified.

4. Apparatus according to claim 2, characterized in that the data storage unit has limit functions $f_{min}(t)$ and $f_{max}(t)$, and the evaluation device is set up for calculating, whether $f_{min}(t) \le f(t) \le f_{max}(t)$ for all $0 \le t \le \Delta t_1$, immediately after the calculation of $f(t)$.

5. Apparatus according to claim 4, characterized in that the evaluation device is set up for calculating the ratio of the averaged slope of $f_{min}(t)$ and $f_{max}(t)$ in the interval $0 \le t \le \Delta t_1$ and the slope of $f(t)$ and for passing on this ratio to the control unit as a multiplier for the laser intensity.

6. Apparatus according to claim 5, characterized in that the control device is set up for switching off the therapeutic laser after the time $t_{coag} > \Delta t_1$ that results as a mean value of the intersections of $f_{min}(t)$ and $f_{max}(t)$ with $F(\Omega_0, t)$.

7. Apparatus according to claim 4, characterized in that the control device is set up to switch off the therapeutic laser, if $f_{min}(t) \le f(t) \le f_{max}(t)$ is not valid for all $0 \le t \le \Delta t_1$.

8. Apparatus according to claim 7, characterized in that the evaluation device is set up for automatically switching on the therapeutic laser with reduced or increased intensity, if $f(\Delta t_1) > f_{max}(\Delta t_1)$ or $f(\Delta t_1) < f_{min}(\Delta t_1)$, and for repeating the fitting procedure.

9. Apparatus according to claim 1, characterized in that the evaluation measure is the maximum amplitude of the optoacoustic signal.

10. Apparatus according to claim 1, characterized in that the evaluation measure is the integral of the absolute value of the optoacoustic signal.

11. Apparatus according to claim 1, characterized in that the evaluation measure is the phase shift of the optoacoustic signals relative to each other.

12. Apparatus according to claim 1, characterized in that the evaluation measure represents the frequency spectrum of the optoacoustic signal and its change.

13. Apparatus according to claim 1, characterized in that the therapeutic laser is designed as a repeatedly pulsed laser having a pulse duration in the range from approximately 1 ns to approximately 10 μm at a repetition rate >100 Hz.

14. Apparatus according to claim 2, characterized in that the value table $F(\Omega, t)$ is determined in a preliminary test from empirical results for the evaluation measure to be used in the therapy.

15. Apparatus according to claim 2, characterized by means for selecting one of several value tables $F(\Omega, t)$ present in the data storage unit.

16. Apparatus according to claim 2, characterized by means for specifying the intended tissue damage $\Omega_0$.

17. Apparatus according to claim 2, characterized by means for selecting the fit function $f(t)$, the fitting parameter, and the time $\Delta t_1$.

18. Apparatus according to claim 17, characterized in that $f(t) = a - b \exp(-\lambda t)$ and a, b, λ can be selected as fitting parameters.

19. Apparatus according to claim 1, characterized in that interval boundaries can be selected for fitting parameters.

20. Apparatus according to claim 4, characterized in that the limit functions can be selected with the selection of the fit function.

* * * * *